United States Patent [19]

Chu et al.

[11] Patent Number: 5,616,595

[45] Date of Patent: Apr. 1, 1997

[54] PROCESS FOR RECOVERING WATER INSOLUBLE COMPOUNDS FROM A FERMENTATION BROTH

[75] Inventors: Alexander H. T. Chu, Buffalo Grove; Gene P. Wloch, Lake Villa, both of Ill.

[73] Assignee: Abbott Laboratories, Abbott Park, Ill.

[21] Appl. No.: 472,615

[22] Filed: Jun. 7, 1995

[51] Int. Cl.$^6$ ................................................. A61K 31/44
[52] U.S. Cl. ........................................................ 514/344
[58] Field of Search ............................................. 514/344

[56] References Cited

U.S. PATENT DOCUMENTS

| | | |
|---|---|---|
| 4,117,118 | 9/1978 | Härri et al. . |
| 4,215,199 | 7/1980 | Härri et al. . |
| 4,231,938 | 11/1980 | Monaghan et al. . |
| 4,346,227 | 8/1982 | Terahara et al. . |
| 4,444,784 | 4/1984 | Hoffman et al. . |
| 4,894,366 | 1/1990 | Okuhara et al. . |
| 5,256,547 | 10/1993 | Rudat et al. ..................... 435/71.1 |

OTHER PUBLICATIONS

Millipore Intertech (1985).
Toso Haas (1989).
Koch Membrane Systems, Inc., "Membranes... The Choice is Yours", Koch, (1994).
Millipore Intertech, "Scaling Up Tangential–Flow Membrane Systems", Millipore, 1–12 (1985).
TosoHaas, "Porous Polymeric Packings for Production Purification of Proteins and Peptides", *Tosohaas Technical Center*, (1989).

*Primary Examiner*—Edward J. Cain
*Attorney, Agent, or Firm*—Andreas M. Danckers

[57] ABSTRACT

A novel process for recovering water insoluble compounds from a fermentation broth includes sequential steps of concentrating, solubilizing and diafiltering the compound of interest, all through a single closed recirculation system to recover the compound for further downstream purification.

20 Claims, 1 Drawing Sheet

5,616,595

PROCESS FOR RECOVERING WATER INSOLUBLE COMPOUNDS FROM A FERMENTATION BROTH

TECHNICAL FIELD

The present invention relates to a novel process for recovering water-insoluble compounds from a fermentation broth. More specifically, this invention relates to a process for recovering cyclosporins and other valuable commercial products from a fermented broth.

BACKGROUND

Various processes have been used in the past to isolate valuable water insoluble commercial compounds from fermentation broths. Traditional technologies for isolating such compounds employ solid-liquid separations (e.g. filtration, centrifugation, etc.) to isolate the water-insoluble active ingredients and subsequent solid-liquid extractions to recover the activities. For example, the U.S. Pat. Nos. 4,117,118 and 4,215,199 to Harri describe processes for isolating cyclosporins A and B from fermentation broths involving the steps of centrifugation, homogenization, and multiple extractions (using methanol, ethylene chloride, and other water-immiscible organic solvents) with corresponding evaporations (i.e. concentrations). Thereafter, the final extracts are subjected to chromatographic purifications using silica gel and SEPHADEX® LH20 packings. Similar procedures are employed for isolating other types of water insoluble compounds such as lovastatin (an antihypercholesterolemic) and tacrolimus (FK-506, an immunosuppressant). Although these methodologies are currently used for industrial scale fermentations, they typically require expensive solid-liquid separators and solvent extractors/evaporators/condensers having high energy requirements. In addition, the product recovery yields from such processes are low due to multi-stage operations. Thus, capital investment and subsequent production costs are high.

As another example, the patent to Rudat (U.S. Pat. No. 5,256,547) describes a process for the production and isolation of cyclosporin A which involves mixing the culture with a filter aid such as recrystallized gypsum or calcite meal to form a suspension and filtering the mixture to obtain a moist biomass. The biomass is then dried and extracted two or three times with a lower carboxylic acid ester, or alternatively with a supercritical gas such as carbon dioxide. The extract is then defatted and chromatographed by preparative HPLC using silica gel or alumina oxide. This method offers limited advantages over those disclosed in earlier patents because it still suffers from multiple, complicated, and expensive operations.

Although the use of either microfiltration (M F) or ultrafiltration (UF) to clarify/filter aqueous fermentation broths has been established in the literature, extractions with organic solvents are usually performed as a secondary purification step to recover the active product. As noted above, the conventional purification procedures involve two distinct unit operations, namely, separation and extraction/evaporation. Generally for water insoluble products, the compound is first isolated from the large volume of aqueous fermentation broth and then purified by repeatedly extracting the compound with solvent and evaporating the solvent, so that the compound can be further extracted with a different solvent and evaporated until a concentration is achieved from which ultimate purification can take place. The repeated extractions and evaporations however, render the process very costly for large scale manufacture.

A unique feature of the present invention is in having a continuous processing system that obviates the need for separate extraction and evaporation steps after the initial centrifugation and/or filtration step. This technology offers many advantages over the prior art processes, including simplicity of design, reduced capital and manufacturing costs, and increased recovery yield. Furthermore, unlike the traditional processes, the entire process of the present invention is both automatable and fully contained which reduces both personnel and environmental exposure to the compound. This is an important consideration in that immunosuppressants and other potent therapeutic compounds may be highly toxic.

SUMMARY

It is therefore an objective of this invention to provide a process for the recovery of water insoluble compounds derived from fermentation broths.

It is another objective of this invention to provide a process for recovering cyclosporins and other drugs from a fermentation broth containing them.

It is another objective of this invention to provide a cheaper process for the large scale recovery of cyclosporins and other drugs from a fermentation broth.

Other objectives of this invention will be apparent to those skilled in the art from the disclosure herein.

Briefly, the invention relates to a process for recovering a water insoluble compound from a raw fermentation broth, comprising the steps of:

a. concentrating the fermentation broth by tangential filtration across a solvent compatible porous filtration membrane, to produce a permeate traversing the membrane and a retentate comprising the concentrated broth, the water insoluble compound being retained in the retentate wherein the retentate continuously recirculates along a circulation path to form a retentate stream, wherein the raw broth is fed into the retentate stream until all of the raw broth is concentrated;

b. solubilizing the water insoluble compound of the retentate by adding a solvent to the concentrated broth to produce a solution of the compound; and c. filtering or diafiltering the solution through the porous membrane of step (a) to produce a solvent permeate traversing the porous membrane wherein the solvent permeate comprises the solubilized compound.

Optionally, the solvent permeate can be further concentrated using a reverse osmosis or ultrafiltration membrane and purified by any method known to those of ordinary skill in the art.

DETAILED DESCRIPTION OF THE INVENTION

Figure 1:
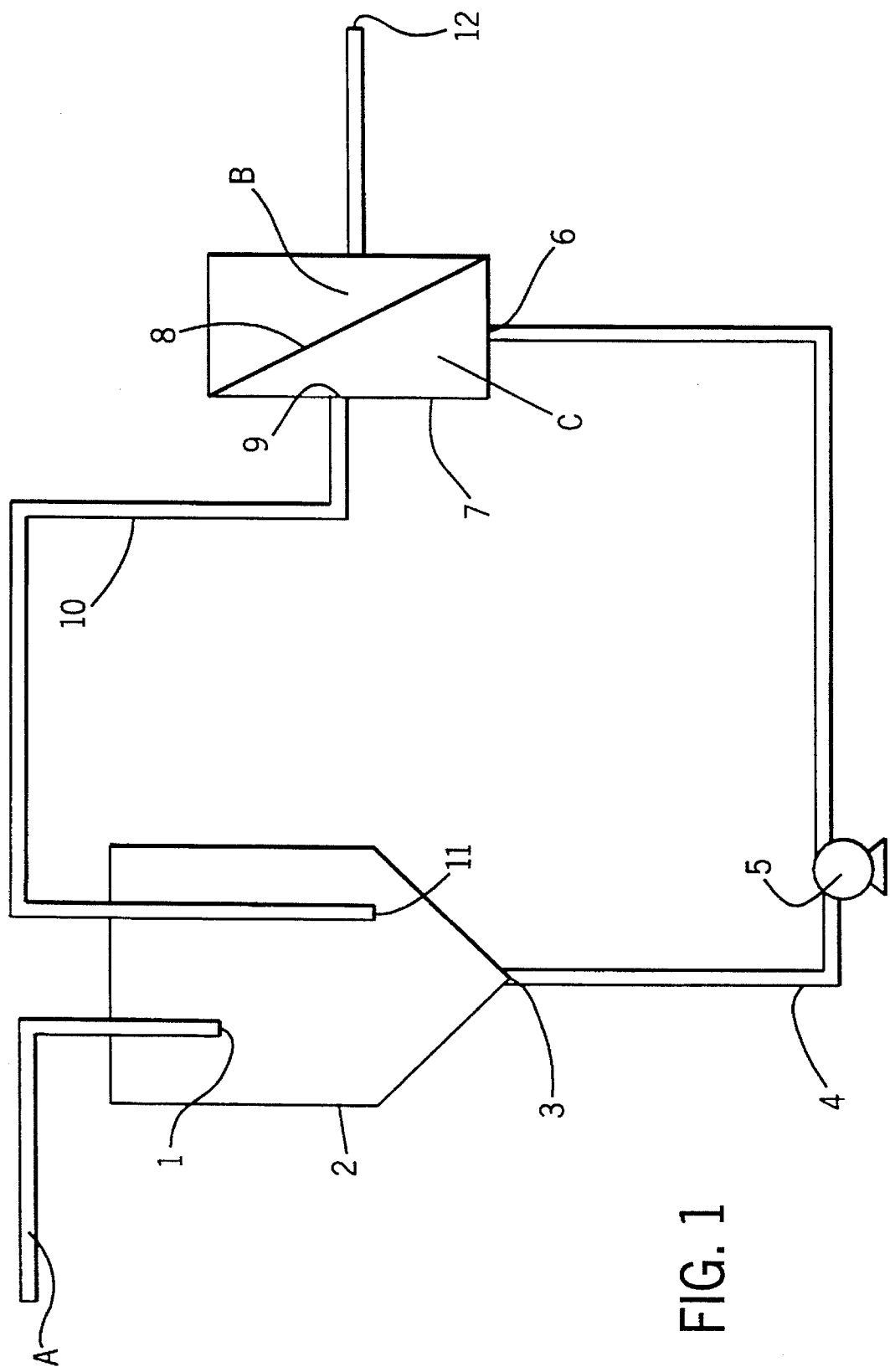
FIG. 1 shows a diagrammatic representation of an embodiment of the invention.

The process of the present invention is directed toward recovering water insoluble compounds that are produced by large scale fermentations. "Recovering" as used herein refers to the process of removing non-compound materials from the compound of interest and encompasses removing excess fluid (eg. concentration by elimination of fermentation broth) and/or removing dissolved or insoluble impurities. Although removing fluid and impurities from the compound of interest results in some purification of the compound, it must be noted that "recovering" does not require achieving any particular degree of purification. That is, recovery does not necessarily result in the compound meeting a defined purification standard (such as an National Formulary, United States Pharmacopeia or European Pharmacopeia specification); rather removal of fluid and impurities in itself is sufficient to achieve recovery.

One proviso to the invention's use, is that the compound itself be insoluble in the fermentation broth at the cessation of the fermentation. "Insoluble compound", as used herein, refers either to any solid compound dispersed in a liquid or gas or to any emulsion of such compound. The insolubility of the compound can result either from the natural properties of the compound itself, or as a consequence of adjusting the solution pH or ionic conditions. For example, immunosuppressants such as cyclosporins are typically produced as insoluble products under fermentation conditions. Certain antibiotic compounds however, such as erythromycin, are typically soluble in the growth medium used to cultivate the production organism, but can be made insoluble at the end of the fermentation process by increasing the broth pH to approximately 8.7–11.0. However, whether the insolubility of the compound is inherent to the compound itself or results from the particular solution conditions, one of ordinary skill in the art would readily understand that the process of the present invention is applicable to any water insoluble compound, existing in suspension or as an emulsion. Examples of water insoluble compounds include, but are not limited to, antibiotics (such as erythromycins A, B, C and D), immunosuppressants (such as cyclosporins A, B and G, rapamycin, ascomycin, or tacrolimus), growth hormones, antihypercholesterolemics (such as lovastatin, pravastatin, or simvastatin) and any intermediates and/or derivatives thereof.

The manner in which the fermentation is performed is not important to the invention, in that any known conditions of fermentation may be utilized. In most circumstances, and particularly for large scale industrial fermentations, the culture medium and fermentation conditions (strain of organism, type of inoculum, time of fermentation, fermentation temperature etc.) are optimized to produce a maximum yield of the desired compound. Examples of suitable fermentation parameters for the production of cyclosporin A and B are described in U.S. Pat. Nos. 4,117,118 and 4,215,199 to Härri et al., and 5,256,547 to Rudat et al.; suitable fermentation parameters for the production of the antihypercholesterolemics lovastatin, simvastatin, pravastatin and the like are described in U.S. Pat. Nos. 4,231,938 to Monaghan et al., 4,444,784 to Hoffman et al. and 4,346,227 to Terahara et al.; and suitable fermentation parameters for the production of the immunosuppressant tacrolimus (FK-506) are described in U.S. Pat. No. 4,894,366 to Okuhara et al., all of which are incorporated herein by reference. For purposes of the present invention, the fermentation process itself may be performed in any small scale or large scale fermentation apparatus, ranging in size from 10 liters to 100,000 liters.

At the cessation of the fermentation, the fermentation broth, containing the desired compound, is contacted with a solvent compatible filtration membrane and filtered by tangential filtration. "Tangential filtration" as used herein, refers to the process of passing a suspension (such as a fermentation broth) across a porous filtration surface in a substantially continuous flow and under pressure so that a large portion of the liquid traverses the filtration membrane. That portion of suspension which traverses the filtration membrane is referred to as "permeate" or "filtrate"; that portion of suspension which does not traverse the membrane is termed "retentate" or "concentrate". The water insoluble compound of interest remains in the retentate. It must be noted that the filtration process does not require the complete removal of all aqueous medium from the insoluble compound, i.e. the retentate may also comprise some residual fermentation broth. However, the remaining aqueous medium may decrease the solubilization efficiency of the solvent in the subsequent step (described below) because of a dilution effect. This may in turn require the use of more solvent to achieve the same degree of concentration efficiency.

The filtration membrane may be made of any material capable of withstanding (i.e. not deteriorating under) the particular solution conditions existing at the end of the fermentation process, i.e. high or low acidity, high or low alkalinity, high or low temperature, high pressure and the like. Furthermore, when the same filtration membrane is used in the subsequent filtration step (see later), it must be "solvent compatible", that is, the filtration membrane must resist degradation when in contact with the particular solvent to be used to solubilize the compound of interest (as is discussed below). Any commercially available filtration membrane may be used for tangential filtration, although surface type or non-depth membranes are preferred. "Surface-type" or "non-depth" membranes are those membranes that retain particulates on their surfaces rather than absorbing or capturing particulates on or within the structural matrix of the membrane. Suitable filtration membranes include organic-solvent compatible polymeric structures made of cellulose, polystyrene, polysulfone or polyamide. Preferred microfiltration membranes are organic-solvent compatible DURAPORE® HVPP membranes (manufactured by Millipore Corporation, Bedford, Mass. 01730) or ceramic structures composed of alumina. A most preferred microfiltration membrane is ceramic alumina. Ceramic alumina filters such as MEMBRALOX®, may be purchased from U.S. Filter Corporation, (181 Thorn Hill Rd., Warrendale, Pa. 15086-7527). Suitable solvent compatible ultrafiltration membranes include PZHK membranes (200,000 molecular weight rating) also available from Millipore Corporation.

The pore size of the first filtration membrane is selected according to the particulate size of the desired insoluble compound contained in the fermentation broth at the end of the fermentation process. Due to their hydrophobic nature, water insoluble compounds either self-aggregate to form particulates in aqueous solution, or form aggregated structures in association with the structures of their respective production organism (eg. cell wall components, mycelia etc.). Thus the pore size of the membrane in the present invention is selected to retain desired insoluble particulates and to allow other smaller sized insoluble matter (when present) as well as soluble compounds to pass through as the aqueous permeate. "Particulate" as used herein, refers either to the desired insoluble compound in a self-aggregated form, or to the desired compound physically and/or chemically associated with any undesired insoluble matter or particle. For example, cyclosporins are physically associated with mycelia at the end of the fermentation process. A similar phenomenon occurs with the immunosuppressant tacrolimus (FK-506). Thus, for these compounds, the pore size is selected to retain the mycelia/compound particulates rather than the specific compound itself.

Filtration membranes of varying pore sizes may be employed in the first filtration step depending on the size of the particulate matter of interest. Preferred microfiltration membranes (particularly for retaining cyclosporin mycelia) have pore sizes ranging from about 0.02 to 5.0 μm, whereas useful ultrafiltration membranes have pore sizes ranging from about 0.001 to about 0.05 μm. It is understood however that one skilled in the art can readily select a suitable membrane for any desired particulate of known size. Furthermore, in the interest of efficiency, it is generally desirable to use the largest pore size that still retains the insoluble particulates (since the larger the pore size, the faster the flux rate, other conditions being equal). Thus, in addition to micro- and ultrafiltration membranes, larger-pored filtration membranes are contemplated within the invention, provided they retain the compound of interest, and are suitable for tangential filtration.

Optionally, other filtration conditions may be optimized (once a filtration membrane has been selected) to enhance the efficiency of processing the compound and to minimize processing costs. For example, having selected a membrane with a particular pore size, other filtration variables such as transmembrane pressure, cross-flow rate and temperature will correlate empirically with a permeate flux rate. (Permeate flux rate, also known as permeation rate, refers to the volume of permeate generated by filtration over a given surface area of membrane and over a given time period. This rate is typically expressed in units of liters/square meters/hour ($L/m^2/hr$). By adjusting the filtration variables, the permeate flux rate may be optimized to reduce the amount of membrane needed. For example, a fermentation broth may have an non-optimized permeate flux rate of 10 $L/m^2/hr$. Thus filtration of 1000 liters of broth in a 10 hour period (100 L/hr), would require 10 $m^2$ of membrane (since 100 L/10 $m^2/hr$=10 $L/m^2/hr$). However, by optimizing the permeate flux rate to 100 $L/m^2/hr$ only 1 $m^2$ of membrane would be required to achieve the same result (ie. filtration of 1000 liters of broth in a 10 hour period). Since the cost of the membrane itself may contribute significantly to the overall cost of processing large volumes of broth, reducing the surface area of the membrane is a particularly important consideration for scaled up operations.

After the initial filtration, the retentate may optionally be diafiltered with approximately two to four volumes of water (relative to retentate) to further remove water soluble impurities. "Diafiltration" or "diafiltering" as used herein refers to a special case of tangential filtration, i.e. to the process of adding a liquid to the retentate at a rate approximately equal to the permeation rate so that the retentate is maintained at a generally constant volume during tangential filtration. "Diafiltrate" is an analogous term to permeate, and refers to that portion of suspension which traverses the membrane during the process of diafiltration. During diafiltration, the residual fermentation broth in the retentate is continuously diluted, so that diafiltration further purifies the desired insoluble compound from the residual soluble contaminants remaining in the broth. Furthermore, depending on the solid content, both the extent of concentration and the volume of diafiltrate can be varied to minimize the possibility of membrane clogging, to reduce process time and to maximize product throughput.

In the second step of the inventive process, the retentate is mixed with a solvent capable of solubilizing the compound of interest to form a solvent slurry. The solvent and its volume are selected so as to preferentially solubilize the compound of interest and minimize solubilization of other insoluble compounds as well as to minimize the extraction of any soluble impurities present in the retentate. Solvents useful in the present invention include alcohols, lower esters, lower ethers, lower ketones and certain chlorinated hydrocarbons such as chloroform and methyl chloride. Preferred solvents include lower alcohols, esters, ether and ketones wherein "lower" refers to straight or branched hydrocarbons of 1–6 carbons. Examples of lower alcohols are methanol, ethanol, propanol, butanol and pentanol; examples of lower esters are methyl acetate, ethyl acetate and methyl butanoate; examples of lower ethers are methyl ethyl ether, diethyl ether and 2-methoxypentane and examples of lower ketones are propanone, 2-butanone and 3-pentanone. Preferred solvents for cyclosporins include lower primary or secondary alcohols and propanone. Those skilled in the art can easily select a suitable solvent knowing the chemical and physical properties of the compound of interest.

The amount of solvent used is generally at least equivalent to the amount of retentate remaining at the end of the first filtration, but may greatly exceed this. Typically, two to six equivalent volumes are used. The efficiency of solubilization is dependent on the solvent volume, i.e. the more solvent used, the more product recovered from the retentate. However, it is also preferable to use as little volume of solvent as possible to minimize the volume of permeate that may need to be concentrated in a further downstream step (as is discussed below).

The solvent is mixed with the retentate for a sufficient time period to solubilize the majority of the water insoluble compound of interest. Although this time period may range from 0 to 24 hours, typical time periods range from about two hours to about six hours. It is understood however that the optimum mixing time may vary, depending on the amount of retentate present, the compound of interest, its solubility in the solvent and the volume of solvent used.

In the third step of the process, the solvent slurry is filtered by tangential filtration through a solvent compatible porous filtration membrane. The filtration membrane is preferably the same filtration membrane as that used in the first step of the process but a fresh or different filtration membrane (provided it is solvent compatible) may also be used. Since the desired compound is now dissolved in solvent, the solvent permeate, rather than the retentate is collected during the filtration process. Although the slurry is ultimately discarded, after permeation, the slurry may optionally be diafiltered with additional solvent. In a manner similar to the aqueous diafiltration described above, solvent diafiltration is achieved by adding solvent to the residual slurry at a rate approximately equal to the permeation rate. In this situation, the additional solvent serves to further extract residual unsolubilized compound remaining in the slurry. The subsequent solvent diafiltrate obtained, is combined with the solvent permeate and constitutes pooled solvent permeate.

Further concentration of the pooled solvent permeate may optionally be achieved by tangentially flitrating it through a solvent compatible membrane having a different pore size than that previously used. The retention membrane used in this step is selected to retain the desired compound based on the compound's solubilized size (ie. molecular weight) rather than its particulate (insoluble aggregate) size and to allow the solvent to pass through the membrane as permeate (which is discarded). Ultrafiltration (UF), nanofiltration (NF) or reverse osmosis (RO) membranes having specific molecular weight cut-offs (MWCO) are employed for this purpose. UF/MWCO membranes suitable for concentrating the collected permeate include regenerated cellulose acetate membranes in a frame and plate or spiral type of configuration, which are commercially available from Millipore Corporation. Suitable NF or RO/MWCO membranes include MPS series SelRO™ cartridges developed by Membrane Products Kiryat Weizmann Ltd. (P.O.B. 138, 76101 Rehovot, Israel) and distributed in the U.S. by LCI Corporation (P.O. Box 16348 Charlotte, N.C. 28297) and also include NANOMAX™ series cellulose acetate spiral wound cartridges also available from Millipore Corporation.

After the concentration on the membrane, the product may optionally be processed further by crystallization or chromatography. In the case of purification by chromatography, the solution can be contacted with a chromatographic medium that selectively retains the compound of interest contained in the solution. Typically such a chromatographic medium is a microporous matrix (prepared from co-polymerization of styrene and divinylbenzene) or a porous silica gel or alumina oxide. The matrix should be of a large enough surface area to bind desired components of the product feed. Chromatography media useful in the present invention include polymeric packings, supports or resins. Examples of such chromatography media include SEPHAROSE®, SEPHADEX® and SEPHACRYL®, (available from Pharmacia Biotech Incorporated, 800 Centennial Ave., P.O. Box 1327, Piscataway, N.J. 08855-1327), DOWEX® series media (available from Dow Chemicals, Midland, Mich.), BIO-REX®, MACROPREP® and BIO-GEL® series media (available from BioRad Laboratories, 85A Marcus Drive, Melville, N.Y. 11747), and Tentacle series packings (available from EM Separations Technology, 350 Columbia St., P.O. Box 352, Wakefield, R.I. 02880). An example of a non-functional polymeric packing is AMBERCHROM™ CG161-m which can be purchased from TosoHaas (Independence Mall West, Philadelphia, Pa. 19105).

As another optional step, the concentrated compound may be purified a second time with a suitable chromatography medium such as silica gel or reverse phase C8 or C18 packings. Suitable chromatography media for such purifications are well known to those of ordinary skill in the art. In a final optional step of the process, the compound can be extracted into another organic solvent, concentrated and crystallized. The crystals are then separated by either filtration or centrifugation and dried under vacuum to obtain the final purified product.

In a preferred embodiment and particularly for large scale fermentations, the isolation of the desired water insoluble compound is accomplished in a closed circulation system as shown in FIG. 1. The fermentation broth (A) is introduced via a first inlet port (1) into the system which comprises a receiving tank (2), a first connecting pipe (4) extending from the outlet port (3) of the receiving tank (2) to the inlet port (6) of the filtration module (7), a pump (5) to pump the fermentation broth (raw or concentrated) through the first connecting pipe (4), a filtration module (7), a filtration membrane (8) housed within the filtration module (7) and a second pipe (10) extending from the outlet port (9) of the filtration module (7) to a second inlet port (11) of the receiving tank (2).

In operation, the raw fermentation broth (A) first enters the receiving tank (2) through an entry port (1), where it flows, under pressure created by the pump (5), into and through the first connecting pipe (4) to the filtration module (7). Within the filtration module (7), the broth contacts the filtration membrane (8). The broth passes across the filtration membrane (8) and is filtered by tangential filtration to produce a permeate (B), which is discarded through an exit port (12) and a retentate (C). The retentate (C) then enters a second connecting pipe (10) extending from the outlet port (9) of the filtration module (7) to the second inlet port (11) of the receiving tank (2). The concentrated broth (C) enters the receiving tank where it is mixed with incoming unconcentrated fermentation broth (A). Thus, the circulating broth forms a retentate stream, flowing unidirectionally through the closed system. In the preferred embodiment, the system is designed to circulate the fermentation broth under approximately 3–50 psi transmembrane pressure (TMP) and at a controlled temperature of approximately 30°–60° C. The broth is circulated through the closed system until approximately ¼ to ½ of the starting broth volume remains as retentate.

In order to minimize the problem of membrane clogging (resulting from concentration of the broth), the system may optionally be designed to incorporate a back pulsation mechanism, which serves to periodically force permeate backwards through the filtration element. As a result of back pulsation, the fouling layer is lifted from the membrane and carried away in the crossflow of retentate. As an alternative or in addition to a back pulsation mechanism, the system design may incorporate any feed and bleed configuration known in the art. Such configurations help prevent local overconcentration of retentate on the membrane. Thus, one skilled in the art can readily adapt the system to prevent membrane clogging by any known method.

It should also be noted that the described operating system may be reconfigured and/or significantly enlarged to accommodate large volumes of broth and to minimize processing costs. For example, the operating system may be designed with numerous filtration modules (in parallel or in series), multiple pumps, conduits and receiving tanks. Large operating systems may be partially or fully automated. Furthermore, large operating systems may incorporate further downstream purification steps as part of an overall recovery/purification scheme. Thus, those individuals having ordinary skill in the chemical engineering arts could readily scale-up or adapt the operating system to conform with available resources (i.e. equipment and space) and to contain manufacturing costs.

In the second step of the process, the permeate exit port (12) of the membrane filtration module (7) is closed. Then, a suitable solvent is added to the retentate in the receiving tank (2), through the same entry port (1) as the raw fermentation broth. The solvent is mixed with the compound of interest for two to six hours until most of the compound is dissolved.

In the next step, the exit port is re-opened and the solvent slurry is recirculated throughout the closed system where it contacts and is filtered through the filtration membrane of the first step. Unlike in the first step, where the aqueous permeate contains little of the compound, the solvent permeate contains most of the compound as dissolved product. Therefore, it is collected continuously in a storage tank for further downstream processing. In the preferred embodiment, once the retentate stream is restarted, fresh solvent is added continuously into the receiving tank to maintain a constant slurry volume. In other words, the solvent slurry is diafiltered with fresh solvent to continuously extract any residual product into the liquid phase. The solvent diafiltrate is then combined with the solvent permeate in the separate storage tank.

At the end of the solvent diafiltration step, the addition of fresh solvent is ceased and the solvent slurry is further concentrated by filtration alone. This step permits a manufacturer to recover the maximum amount of the product from the slurry before discarding the spent slurry as waste.

If necessary, a fourth step can be designed in such a way that water can be added to the spent slurry concentrate to recover residual solvent which may not be desirable for anaerobic waste treatment (since the presence of organic solvent usually increases the BOD (biological or biochemical oxygen demand). Also, the solvent recovered from this washing step can be recycled or distilled for re-use to minimize the environmental impact. This then completes the three cycles of membrane operations which are summarized in Table 1 below:

TABLE 1

| Cycle No. | Process | Feed | Retentate | Permeate |
|---|---|---|---|---|
| 1 | Concentration of compound | Fermentation broth | Broth (product) | Aqueous waste |
| 1a* | Diafiltration | Water | Broth (product) | Aqueous waste |
| 2 | Solubilization/ Mixing | Solvent | Slurry (product) | None |
| 3 | Filtration | None | Slurry (residual product) | Clarified liquid (product) |
| 3a* | Diafiltration | Fresh solvent | Slurry (residual product) | Clarified liquid (product) |
| 3b* | Concentration of slurry | None | Slurry (residual product) | Clarified liquid (product) |
| 4* | Wash | Water | Spent slurry | Recovered solvent |

*refers to optional steps

The pooled solvent permeate (i.e. solvent permeate plus solvent diafiltrate) is subsequently concentrated using a Millipore NANOMAX™ series spiral wound RO cartridge. Afterward, the concentrate may be further purified by recrystallization or chromatography. In a typical example, an AMBERCHROM™ CG161-m column is charged with a quantity of crude cyclosporin concentrate and the bed is eluted with an ethanol-water gradient (20–60%). Individual fractions are analyzed by high performance liquid chromatography (HPLC) or thin layer chromatography (TLC) to determine the fractions containing compound activity. The chromatographed solution and/or all pooled fractions of eluant therefrom, may then be concentrated either by ultrafiltration or reverse osmosis and further purified by any methods known to those of ordinary skill in the art. The concentrated solution may also be extracted with a suitable solvent to prepare for final purification.

The invention will now be described further by way of examples. The examples are merely illustrative of the invention and are not intended to limit the invention in any way.

EXAMPLE 1

Recovery of Cyclosporins Microfiltration and Methanol Extraction

Approximately 160 liters of cyclosporin fermentation broth from Run CD-263 containing 5.1% dried solids and 10% suspended wet solids was fed into a receiving tank. The membrane unit consisted of two 0.2 μm ROMICON® (Koch Membrane Systems, Inc., 850 Main Street, Wilmington, Mass. 01887) ceramic microfiltration (CMF) membrane elements (in series), each having a surface area of 0.2 m². The inlet pressure was set at 60 psi and the broth was recirculated through the system while the aqueous permeate containing the water-soluble impurities was removed. After 90 minutes, during which time the average permeate flux rate was 183 $L/m^2/hr$, the volume was concentrated to approximately 50 liters. Then, fresh water was added to the receiving tank at the same rate as the permeation rate to continue the removal of water and associated impurities, The permeate flux rate was measured at approximately 150 $L/m^2/hr$. Approximately 155 liters of permeate and diafiltrate were collected and sampled by HPLC; little cyclosporin activity was detected in the sample.

As a second step, 100 liters of methanol was added to the receiving tank which contained 50 liters of concentrated broth (diafiltered), the valve to the membrane was closed and the slurry was mixed for two hours. The CMF unit was restarted and the dissolved product was separated by the membrane (ie. as permeate) and collected in a product tank. The permeate flux rate started at 105 $L/m^2/hr$ under pressure of 60 psi (inlet) and 32 psi (outlet) and slowly decreased to 36 $L/m^2/hr$. The pressure was then increased to approximately 80 psi (inlet) and 55 psi (outlet) while the temperature was maintained at 28°–30° C. After concentrating the slurry to 100 liters, 20 liters of methanol wash was added (in order to increase the cyclosporin yield). About 27 grams (64%) of cyclosporin was recovered while 15 grams (36%) was still present in the retentate after the methanol wash, as determined by HPLC.

EXAMPLE 2

Recovery of Cyclosporins by Ceramic Microfiltration and Methanol/Ethyl Acetate Extraction Approximately 8 liters of cyclosporin fermentation broth from Run CD-265 containing 4.6% dried solids was fed into a receiving tank. The membrane unit consisted of one 0.2 μm Millipore CERAFLO® ceramic microfiltration (CMF) membrane element having a 0.12 m² surface area. The outlet pressure was set at 20–30 psi and the inlet pressure at 50–55 psi. The broth was recirculated through the system while the aqueous permeate containing the water-soluble impurities was removed. The initial permeate flux rate across the membrane was 450 $L/m^2/hr$ and slowly decreased to 100 $L/m^2/hr$ after 30 minutes of filtration. The volume was concentrated to approximately 2 liters and another 8 liters of fresh broth was added, which was further concentrated to approximately 2 liters. The permeate flux rate decreased to about 50 $L/m^2/hr$. Then, a total of 12 liters of distilled water was added in 2 liter aliquots to the tank at the same rate as the permeation rate (diafiltration) to continue the removal of water and associated impurities. The flux rate was measured at approximately 50–65 $L/m^2/hr$.

As a second step, the valve to the membrane was closed and 2 liters of methanol was added to the receiving tank; the slurry was then mixed for two hours. An additional 2 liters of methanol/ethyl acetate (50/50 v/v) was added before the CMF unit was restarted. The cyclosporin product, dissolved in the methanol/ethyl acetate solvent was diafiltered through the membrane and collected in a product tank. The flux rate started at 75 $L/m^2/hr$ under pressure of 48 psi (inlet) and 26 psi (outlet) and slowly increased to 155 $L/m^2/hr$ upon diafiltration with a total of 16 liters of methanol/ethyl acetate. The temperature was not controlled and fluctuated between 28°–36° C. during solvent diafiltration.

EXAMPLE 3

Methanol Extraction of Cyclosporin A Using a Niro® 0.05 μm Ceramic Membrane

Approximately 140 liters of cyclosporin fermentation broth from Run CD-268 containing 11.3% dried solids and 26% suspended wet solids was fed into a receiving tank. The membrane unit consisted of one 0.05 μm Niro® ceramic microfiltration (CMF) membrane element having 0.3 m² surface area, and 6 millimeter (mm) diameter channels. The inlet pressure was set at 60 psi and the broth was recirculated through the system while the aqueous permeate containing the water-soluble impurities was removed. The initial permeate flux rate across the membrane was 246 L/m$^2$/hr and slowly decreased to 48 L/m$^2$/hr after 90 minutes. The volume of broth was concentrated to approximately 58 liters, then 72 liters of distilled water was added to the receiving tank to continue the removal of water and associated impurities. The permeate flux rate increased to approximately 220–280 L/m$^2$/hr due to the dilution effect. After concentrating the diluted broth to 40 liters, an additional 90 liters of distilled water was added to continue the broth wash. The collected permeate was analyzed by HPLC and showed little activity (approx. 0.002 grams/L of cyclosporin A). When the broth (retentate) was concentrated to 38 liters, the ceramic unit was stopped and 92 liters of methanol was added and mixed for approximately 14 hours to dissolve the cyclosporin into the alcohol phase.

The CMF unit was restarted and the product dissolved in the methanol permeate was separated by the membrane and collected in a product tank. The solvent permeate flux rate started at 50 L/m$^2$/hr under pressure of 68–70 psi (inlet) and 38–40 psi (outlet) and slowly decreased to 14 L/m$^2$/hr. The temperature started at 35° C. and slowly increased to about 50° C. from heat generated by recirculation. A total of 70 liters of methanol containing the product was collected for further processing.

EXAMPLE 4

Ethanol Extraction of Cyclosporin A Using a Niro® 0.05 μm Ceramic Membrane

Approximately 30,500 L of fermentation broth from Run-102 was pumped into a receiving tank which fed (four recirculation loops each containing four) in series Niro® ceramic microfiltration (CMF) modules (housing 0.05 μm membranes with a total of 60 m$^2$ surface area for the system). The transmembrane pressures were controlled at approximately 5 to 15 psi and the feed temperatures were controlled at 35° C. to 45° C. The permeate flux rates ranged from 23 L/m$^2$/hr to 62 L/m$^2$/hr. The material was concentrated to 9,000 L and with approximately 24,000 L of water. The permeate. flux rates of the ranged from 44 L/m$^2$/hr to 70 L/m$^2$/hr. The material was concentrated to a final volume of 8,100 L. Approximately 10,900 L of Specially Denatured 3A grade ethyl alcohol was then added to the concentrate and heated to 35° C. to 40° C. for two hours. The solvent slurry was diafiltered with an additional 19,000 L of Specially Denatured 3A grade ethyl alcohol. The slurry was concentrated to a final volume of approximately 6,500 L and contained less than 5% of the raw broth activity as determined by HPLC. Approximately 35,000 L of solvent permeate was collected and subsequently concentrated by reverse osmosis as described in Example 5 below.

EXAMPLE 5

Concentration of Cyclosporin A Using a Millipore NANOMAX™-50 Reverse Osmosis Membrane Approximately 35,000 L of cyclosporin enriched ethanol solution from Run-102 was fed to a Millipore reverse osmosis unit containing 180 m$^2$ total surface area of NANOMAX™-50 membranes. The membranes are compatible with up to 70% ethanol (by weight), so the feed stream was partially diluted with water and clarified by filtration prior to feeding the reverse osmosis unit. The material was pumped from a feed tank to a high-pressure multistage pump. The product was pumped across the membranes at crossflow rates of 120–170 L/min. and the retentate was returned to the feed tank. The transmembrane pressure was typically controlled at 500 psi with the temperature controlled at 39° C.–47° C. The permeate flux rates ranged from 3.3–15.3 L/m$^2$/hr. The permeate from the reverse osmosis contained only residual cyclosporin activity and was discarded.

EXAMPLE 6

Further Concentration of Cyclosporin A Using Millipore 1000 MWCO PLAC Series Ultrafiltration Membrane Approximately 20 liters of methanol permeate containing cyclosporin A from the ceramic microfiltration of fermentation broth (Run CD-273) were placed in a feed tank of a Millipore PROSTAK™ ultrafiltration system. One 0.93 m$^2$ of PLAC regenerated cellulose membrane with about a 1,000 MWCO was used in a tangential flow, plate and frame type of module. The stream temperature was maintained at 28°–30° C. using a heat exchanger with cooling water. The inlet and outlet pressures were controlled at approximately 80 psi and 68 psi respectively, and the transmembrane pressure (TMP) was controlled at about 55 psi. The permeate flux rate started at 11.6 L/m$^2$/hr and finished at 8.4 L/m$^2$/hr after a 5-fold concentration (i.e. 4 liters of final retentate). The product was retained in the retentate and methanol removed in the permeate. The typical yield of product for this membrane concentration step was about 94% with 6% of product lost in the permeate. Afterwards, the system was flushed and cleaned with fresh methanol followed by distilled water to restore the initial flux rate.

We claim:

1. A process for recovering within a single apparatus a water insoluble compound from a raw fermentation broth, comprising the steps of:

a. concentrating said fermentation broth by tangential filtration across a solvent compatible porous filtration membrane, to produce a permeate traversing said membrane and a retentate comprising said concentrated broth, said water insoluble compound being retained in said retentate wherein said retentate continuously recirculates along a circulation path to form a retentate stream, wherein said raw broth is fed to said retentate stream until all of said raw broth is concentrated;

b. solubilizing said water insoluble compound of said retentate by adding a solvent to said concentrated broth to produce a solution of said compound; and c. filtering or diafiltering said solution through said filtration membrane of step (a) to produce a solvent permeate traversing said filtration membrane wherein said solvent permeate comprises said solubilized compound.

2. The process of claim 1 wherein said compound is selected from the group consisting of an immunosuppressant, a macrolide antibiotic, an antihypercholesterolemic, a cyclosporin, and their derivatives and intermediates.

3. The process of claim 2 wherein said compound is an immunosuppressant selected from cyclosporin A, cyclosporin B, cyclosporin G, rapamycin, ascomycin, and tacrolimus.

4. The process of claim 3 wherein said immunosuppressant is cyclosporin A.

5. The process of claim 3 wherein said immunosuppressant is cyclosporin B.

6. The process of claim 3 wherein said immunosuppressant is cyclosporin G.

7. The process of claim 2 wherein said compound is an antihypercholesterolemic selected from lovastatin, pravastatin, simvastatin and fluvastatin.

8. The process of claim 2 wherein said compound is a macrolide antibiotic selected from erythromycin's A, B, C and D.

9. The process of claim 1 wherein said filtration membrane has a pore size of about 0.001 μm to about 5.0 μm.

10. The process of claim 1 wherein said filtration membrane has a pore size of about 0.001 μm to about 0.05 μm.

11. The process of claim 1 wherein said filtration membrane has a pore size of about 0.02 μm to about 5.0 μm.

12. The process of claim 1 wherein said filtration membrane is selected from the group consisting of cellulose, polystyrene, polysulfone and polyamide.

13. The process of claim 1 wherein said filtration membrane is ceramic alumina.

14. The process of claim 13 wherein said filtration membrane has a pore size of about 0.05 μm to about 5.0 μm.

15. The process of claim 1 wherein said solvent of step b is selected from the group consisting of lower alcohol, lower ester, lower ether, and lower ketone.

16. The process of claim 15 wherein said solvent is an alcohol selected from methanol, ethanol, propanol and butanol.

17. The process of claim 1 further comprising the step of diafiltering said concentrated broth through said filtration membrane of step (a) prior to solubilizing said compound in step (b).

18. The process of claim 1 further comprising the step of concentrating said solvent permeate on a reverse osmosis or ultrafiltration membrane.

19. The process of claim 18 wherein said reverse osmosis membrane is a NANOMAX™-50 spiral cartridge.

20. The process of claim 18, further comprising the steps of recrystallization, silica gel chromatography and centrifugation.

* * * * *